US007820167B2

(12) United States Patent
Donovan et al.

(10) Patent No.: US 7,820,167 B2
(45) Date of Patent: Oct. 26, 2010

(54) IL1-β: A NEW TARGET FOR MYELOMA THERAPY

(75) Inventors: Kathleen A. Donovan, Rochester, MN (US); John A. Lust, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1363 days.

(21) Appl. No.: 11/043,209

(22) Filed: Jan. 26, 2005

(65) Prior Publication Data

US 2005/0164312 A1 Jul. 28, 2005

Related U.S. Application Data

(62) Division of application No. 09/821,719, filed on Mar. 29, 2001, now Pat. No. 6,864,047.

(51) Int. Cl.
*A61K 39/395* (2006.01)
*A61K 38/16* (2006.01)
*A61K 38/20* (2006.01)

(52) U.S. Cl. ................ 424/145.1; 424/85.2; 424/134.1; 514/2

(58) Field of Classification Search ................ 424/85.2, 424/130.1, 143.1
See application file for complete search history.

(56) References Cited

U.S. PATENT DOCUMENTS

| 4,946,778 | A | 8/1990 | Ladner et al. |
| 5,470,952 | A | 11/1995 | Stahl et al. |
| 5,844,099 | A | 12/1998 | Stahl et al. |

FOREIGN PATENT DOCUMENTS

WO   WO 98/03657   1/1998

OTHER PUBLICATIONS

Lust et al., "Interleukin-1 receptor antagonist (IL-1Ra) targets the proliferative component in early stage myeloma," *Blood* (ASH Annual Meeting Abstracts), 2004, 104:Abstract 2412.
Lust et al., "Clinical and biologic studies in smoldering/indolent multiple myeloma (SMM/IMM) suggest that therapies that specifically inhibit IL-6 production are more effective at targeting the proliferative myeloma component than apoptosis inducing agents," *Blood* (ASH Annual Meeting Abstracts), 2006, 108:Abstract 3500.
Lust et al., "Prevention of active multiple myeloma (MM) using IL-1 receptor anatagonist (IL-1ra) and low-dose dexamethasone (Dex) and monitoring the high sensitivity C-reactive protein (hsCRP)," *J. Clin. Oncol.*, 2007 ASCO Annual Meeting Proceedings Part I. vol. 25, No. 18S (Jun. 20 Supplement), 2007:Abstract 8105.
Famularo et al., "The role of cytokines in the pathogenesis of monoclonal gammapathies," *EOS-Rivista Di Immunologia Ed Immunofarmacologia*, 1993, 13:176-185, Abstract only.
Wallace et al., "Abnormalities of bone marrow mesenchymal cells in multiple myeloma patients," *Cancer*, 2001, 91(7):1219-1230, Abstract only.
Vacca et al., "A Disturbance of the IL-2-IL-2 Receptor System Parallels the Activity of Multiple Myeloma," *Clin. Exp. Immunol.*, 1991, 84(3):429-434, Abstract only.
"Human Interleukin-6 UltraSensitive (hIL-6 US) ELISA Kit," Summary Protocol, BioSource International, Inc., pp. 1-2.
Alexanian and Dimopoulos, "The Treatment of Multiple Myeloma," *New Engl. J. Med.*, 1994, 330(7):484-489.
Attal et al., "A Prospective, Randomized Trial of Autologous Bone Marrow Transplantation and Chemotherapy in Multiple Myeloma," *N. Engl. J. Med.*, 1996, 335:91-97.
Bataille et al., "Clinical Evaluation of Response or Escape to Chemotherapy and of Survival of Patients with Multiple Myeloma. A Prospective Study of 202 Patients (1975-1982)," *Anticancer Research*, 1984, 4:339-346.
Bataille et al., "Serum Levels of Interleukin 6, a Potent Myeloma Cell Growth Factor, as a Reflect of Disease Severity in Plasma Cell Dyscrasias," *J. Clin. Invest.*, 1989, 84:2008-2011.
Bataille et al., "Biologic Effects of Anti-Interleukin-6 Murine Monoclonal Antibody in Advanced Multiple Myeloma," *Blood*, 1995, 86(2):685-691.
Borset et al., "Lack of IL-1 secretion from human myeloma cells highly purified by immunomagnetic separation," *Br. J. Haematology*, 1993, 85:446-451.
Carter et al., "The role of interleukin-1 and tumour necrosis factor-α in human multiple myeloma," *Br. J. Haematol.*, 1990, 74:424-431.
Carter et al., "Purification, cloning, expression and biological characterization of an interleukin-1 receptor antagonist protein," *Nature*, 1990, 344:633-638.
Chauhan et al., "Multiple Myeloma Cell Adhesion-Induced Interleukin-6 Expression in Bone Marrow Stromal Cells Involves Activation of NF-κB," *Blood*, 1996, 87(3):1104-1112.
Choi et al., "Macrophage inflammatory protein 1-alpha is a potential osteoclast stimulatory factor in multiple myeloma," *Blood*, 2000, 96(2):671-675.
Cole et al., "The EBV-Hybridoma Technique and Its Application to Human Lung Cancer," *Monoclonal Antibodies and Cancer Therapy*, Alan R. Liss, Inc., 1985, pp. 77-96.
Cote et al., "Generation of human monoclonal antibodies reactive with cellular antigens," *Proc. Natl. Acad. Sci. USA*, 1983, 80:2026-2030.
Costes et al., "Interleukin-1 in multiple myeloma: producer cells and their role in the control of IL-6 production," *Br. J. Haematol.*, 1998, 103:1152-1160.

(Continued)

*Primary Examiner*—Mary E Mosher
*Assistant Examiner*—Myron G Hill
(74) *Attorney, Agent, or Firm*—Fish & Richardson P.C.

(57) ABSTRACT

Diagnostic methods for the detection of multiple myeloma (MM) and the identification of high-risk patients with multiple myeloma-related plasma proliferative disorders, such as MGUS or SMM, likely to progress to active MM are described. The diagnosis is based on the determination of concentrations of bioactive IL-1β produced by the bone marrow plasma cells of these patients. Also described are therapeutic methods for the treatment of MM and for the chemoprevention of the progression from disorders such as MGUS and SMM to active MM, involving the administration of inhibitors of IL-1β.

34 Claims, 7 Drawing Sheets

OTHER PUBLICATIONS

*Cytokines: A Practical Approach*, 1991, Balkwill (ed.), Oxford University Press, pp. 311-312.

Dankbar et al., "Vascular endothelial growth factor and interleukin-6 in paracrine tumor-stromal cell interactions in multiple myeloma," *Blood*, 2000, 95(8):2630-2636.

Dinarello et al., "Anticytokine Strategies in the Treatment of the Systemic Inflammatory Response Syndrome," *JAMA*, 1993, 269(14):1829-1835.

Dinarello, "Biologic Basis for Interleukin-1 in Disease," *Blood*, 1996, 87(6):2095-2147.

Dinarello and Thompson, "Blocking IL-1: interleukin 1 receptor antagonist in vivo and in vitro," *Immunol. Today*, 1991, 12(11):404-410.

Donovan et al., "Contrast in cytokine expression between patients with monoclonal gammopathy of undetermined significance or multiple myeloma," *Leukemia*, 1998, 12:593-600.

Donovan et al., "Stromal Cell Interleukin-6 (IL-6) Production and Percent Plasma Cells Predict Progression of Smoldering Multiple Myeloma (SMM) to Multiple Myeloma (MM): Importance of the IL-1β/IL-6 Axis in Myeloma Pathogenesis," *44th ASH Annual Meeting*, 2002, 2 pages.

Eisenberg et al., "Primary structure and functional expression from complementary DNA of a human interleukin-1 receptor antagonist," *Nature*, 1990, 343:341-346.

Fingl and Woodbury, "General Principles," *The Pharmaceutical Basis of Therapeutics*, 1975, MacMillan Publishing Co., New York, Chapter 1, pp. 1-46.

Greipp and Lust, "Pathogenetic Relation Between Monoclonal Gammopathies of Undetermined Significance and Multiple Myeloma," *Stem Cells*, 1995, 13(Suppl. 2):10-21.

Greipp and Witzig, "Biology and treatment of myeloma," *Curr. Opn. Oncol.*, 1996, 8:20-27.

Grigorieva et al., "The bone marrow stromal environment is a major factor in myeloma cell resistance to dexamethasone," *Exp. Hematol.*, 1998, 26:597-603.

Hannum et al., "Interleukin-1 receptor antagonist activity of a human interleukin-1 inhibitor," *Nature*, 1990, 343:336-340.

Hawley et al., "Expression of Retrovirally Transduced IL-1α in IL-6-Dependent B Cells: A Murine Model of Aggressive Multiple Myeloma," *Growth Factors*, 1991, 5:327-338.

Hilbert et al., "Interleukin 6 Is Essential for In Vivo Development of B Lineage Neoplasms," *J. Exp. Med.*, 1995, 182:243-248.

Howard et al., "IL-1-Converting Enzyme Requires Aspartic Acid Residues for Processing of the IL-1β Precursor at Two Distinct Sites and Does Not Cleave 31-kDa IL-1α," *J. Immunol.*, 1991, 147(9):2964-2969.

Huse et al., "Generation of a Large Combinatorial Library of the Immunoglobulin Repertoire in Phage Lambda," *Science*, 1989, 246:1275-1281.

Kawano et al., "Autocrine generation and requirement of BSF-2/IL-6 for human multiple myelomas," *Nature*, 1988, 332:83-85.

Kishimoto, "The Biology of Interleukin-6," *Blood*, 1989, 74:1-10.

Kiss et al., "Determination of IL6, Ill and IL4 in the Plasma of Patients with Multiple Myeloma," *Leukemia and Lymphoma*, 1994, 14:335-340.

Klein et al., "Paracrine Rather Than Autocrine Regulation of Myeloma-Cell Growth and Differentiation by Interleukin-6," *Blood*, 1989, 73(2):517-526.

Klein et al., "Inhibiting IL-6 in Human Multiple Myeloma," *Curr. Topics Microbiol. Immunol.*, 1992, 182:237-244.

Köhler and Milstein, "Continuous cultures of fused cells secreting antibody of predefined specificity," *Nature*, 1975, 256:495-497.

Kozbor and Roder, "The production of monoclonal antibodies from human lymphocytes," *Immunology Today*, 1983, 4:7279.

Kyle, "Newer Approaches to the Management of Multiple Myeloma," *Cancer*, 1993, 72(11):3489-3494.

Kyle, ""Benign" Monoclonal Gammopathy—After 20 to 35 Years of Follow-up," *Mayo Clin. Proc.*, 1993, 68:26-36.

Kyle and Greipp, "Smoldering Multiple Myeloma," *New Engl. J. Med.*, 1980, 302:1347-1349.

Kyle and Lust, "Monoclonal Gammopathies of Undetermined Significance," *Sem. Hematol.*, 1989, 26(3):176-200.

Lacy et al., "Comparison of Interleukin-1β Expression by In Situ Hybridization in Monoclonal Gammopathy of Undetermined Significance and Multiple Myeloma," *Blood*, 1999, 93:300-305.

Lust and Donovan, "Biology of the Transition of Monoclonal Gammopathy of Undetermined Significance (MGUS) to Multiple Myeloma," *Cancer Control*, 1998, 5(3):209-217.

Lust and Donovan, "The Role of Interleukin-1β in the Pathogenesis of Multiple Myeloma," *Hematology/Oncology Clinics of North America*, 1999, 13(6):1117-11125.

March et al., "Cloning, sequence and expression of two distinct human interleukin-1 complementary DNAs," *Nature*, 1985, 315:641-647.

Nagata et al., "Interleukin 1 Autocrine Growth System in Human Multiple Myeloma," *Jpn. J. Clin. Oncol.*, 1991, 21:22-29.

Oken et al., "Comparison of Melphalan and Prednisone with Vincristine, Carmustine, Melphalan, Cyclophosphamide, and Prednisone in the Treatment of Multiple Myeloma," *Cancer*, 1997, 79:1561-1567.

Parker et al., "Cancer Statistics, 1996," *CA Cancer J. Clin.*, 1996, 46:5-27.

Portier et al., "In vivo interleukin 6 gene expression in the tumoral environment in multiple myeloma," *Eur. J. Immunol.*, 1991, 21:1759-1762.

Sati et al., "Expression of interleukin-1β and tumour necrosis factor-α in plasma cells from patients with multiple myeloma," *Br. J. Haematology*, 1999, 104:350-357.

Schindler et al., "Dissociation Between Interleukin-1β mRNA and Protein Synthesis I Human Peripheral Blood Mononuclear Cells," *J. Biol. Chem.*, 1990, 265(18):10232-10237.

Schwab et al., "Characterization of an Interleukin-6-Mediated Autocrine Growth Loop in the Human Multiple Myeloma Cell Line, U266," *Blood*, 1991, 77(3):587-593.

Singhal et al., "Antitumor Activity of Thalidomide in Refractory Multiple Myeloma," *N. Engl. J. Med.*, 1999, 341:1565-1571 and correction in *N. Engl. J. Med.*, 2000,342(5):364.

Sleath et al., "Substrate Specificity of the Protease That Processes Human Interleukin-1β," *J. Biol. Chem.*, 1990, 265(24):14526-14528.

Tanihara et al., "A Synthetic Peptide Corresponding to 86-93 of the Human Type I IL-1 Receptor Binds Human Recombinant IL-1 (α and β) and Inhibits IL-1 Actions in vitro and in vivo," *Biochem. Biophys. Res. Comm.*, 1992, 188(2):912-920.

Thomas et al., "Interdependence between Cytokines and Cell Adhesion Molecules to Induce Interleukin-6 Production by Stromal Cells in Myeloma," *Leukemia and Lymphoma*, 1998, 32:107-119.

Torcia et al., "Modulation of osteoclast-activating factor activity of multiple myeloma bone marrow cells by different interleukin-1 inhibitors," *Exp. Hematol.*, 1996, 24:868-874.

Yamamoto et al., "Production of Interleukin 1β, a Potent Bone Resorbing Cytokine, by Cultured Human Myeloma Cells," *Cancer Res.*, 1989, 49:4242-4246.

Zhang et al., "Interleukin-6 Is a Potent Myeloma-Cell Growth Factor in Patients With Aggressive Multiple Myeloma," *Blood*, 1989, 74:11-13.

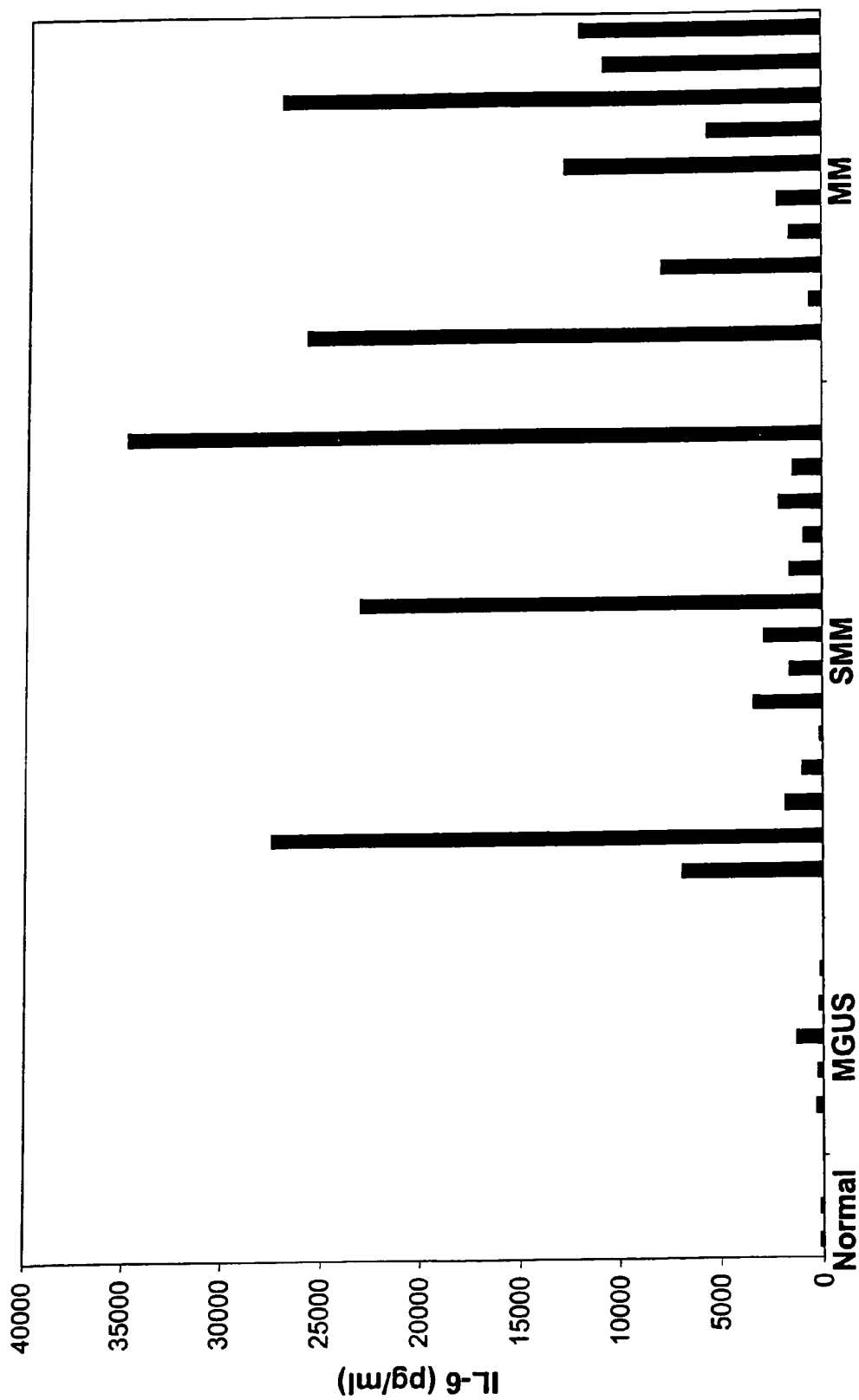

IL1-β: A NEW TARGET FOR MYELOMA THERAPY

CROSS-REFERENCE TO RELATED APPLICATIONS

This application is a divisional of U.S. Ser. No. 09/821,719, filed Mar. 29, 2001 now U.S. Pat. No. 6,864,047.

STATEMENT AS TO FEDERALLY SPONSORED RESEARCH

This invention was made with Government support from the National Institutes of Health. The Government has certain rights in the invention.

BACKGROUND OF THE INVENTION

The present invention relates generally to the observation of a correlation between the production of bioactive IL-1β by bone marrow cells and the clinical features of multiple myeloma.

Despite aggressive treatment approaches, multiple myeloma (MM) is a universally fatal B cell malignancy, accounting for 1-2% of all cancer deaths. See Silverberg et al. (1996) *Ca. J. Clin.* 46: 5-27. MM is recognized clinically by the proliferation of malignant plasma cells in the bone marrow, the detection of a monoclonal protein (M protein) in the serum or urine, anemia, hypercalcemia, renal insufficiency and lytic bone lesions. See Kyle and Lust (1989) *Seminars in Hematology* 26: 176-200. Several multiple myeloma-related plasmaproliferative disorders, such as monoclonal gammopathy of undetermined significance (MGUS) and smoldering multiple myeloma (SMM), are characterized by the detection of M protein in the serum or urine without the other clinical features of MM. MGUS, a clinically benign precursor condition of MM is more common than MM, occurring in 1% of the population over age 50 and 3% of those over age 70. Greipp and Lust (1995) *Stem Cells* 13: 10-21. It is of great clinical importance to distinguish patients with MGUS from those with MM, as MGUS patients may be safely observed without resort to chemotherapy. The unnecessary treatment of MGUS patients can lead to acute leukemia or morbidity/mortality from chemotherapy. However, during long-term follow-up, of 241 patients with MGUS, 59 patients (24.5%) went on to develop MM or a related disorder. See Kyle (1993) *Mayo Clinic Proceedings* 68: 28. Thus, the prevention of myeloma from MGUS would have a significant impact on the morbidity and mortality of myeloma.

Chemotherapy and peripheral blood stem cell transplant are the treatments for symptomatic patients with active MM. Patients who are candidates for peripheral blood stem cell harvest typically receive four cycles of VAD (vincristine, doxorubicin [Adriamycin] and dexamethasone) chemotherapy followed by peripheral blood cell harvest. Subsequently, myeloma patients either continue on standard chemotherapy such as VBMCP (vincristine, carmustine [BCNU], melphalan, cyclophosphamide and prednisone) or proceed directly to transplant. See Attal et al. (1996) *N. Engl. J. Med.* 335: 91 and Alexanian and Dimopoulos (1994) *N. Engl. J. Med.* 330: 484. Patients who are not candidates for transplantation receive standard chemotherapy consisting of either VBMCP or melphalan in combination with prednisone. See Oken et al. (1997) *Cancer* 79: 1561. Recently, thalidomide has been shown to have activity in patients with recurrent myeloma. See Singhal et al. (2000) *N. Engl. J. Med.* 2000; 342(5): 364 and Singhal et al. (1999) *N. Engl. J. Med.* 341: 1565. Chemotherapy is usually continued until the patient has reached a plateau state, which is defined as a stable M protein in the serum and urine and no evidence of progression of myeloma. In most patients, chemotherapy plus analgesics can control the bone pain characteristic of the disease. The duration of survival of patients with MM ranges from a few months to many years with the median survival of 2.5-3 years. See Oken et al., supra. Even with transplantation, except for a rare patient, all patients eventually relapse and succumb to their disease. See Attal et al. supra.

Newer therapeutic strategies for MM are clearly needed. The prevention or delay of the progression to MM from related plasmaproliferative disorders, such as MGUS and SMM, with an effective chemotherapeutic agent would have a major impact on the treatment of patients with plasmaproliferative disorders.

SUMMARY OF THE INVENTION

The invention is based on the discovery that bioactive IL-1β, while undetectable in normal plasma cells, is abnormally expressed in the plasma cells of virtually all myeloma patients and approximately 25% of patients with related plasma proliferative disorders, such as MGUS or SMM. The invention includes diagnostic methods for the detection of MM and the identification of high-risk MGUS and SMM patients likely to progress to active MM. The diagnosis is based on the determination of concentrations of bioactive IL-1β produced by the bone marrow plasma cells of these patients. The invention also includes therapeutic methods for the treatment of myeloma and for the chemoprevention of the progression from multiple myeloma-related plasmaproliferative disorders, such as MGUS or SMM, to active MM, involving the administration of inhibitors of IL-1β.

In general, the invention features a method of quantitating IL-1β in a bone marrow preparation including culturing stromal cells with the bone marrow preparation, determining the amount of IL-6 produced by the stromal cell culture and correlating the amount of IL-6 produced to the IL-1β concentration in the bone marrow preparation by comparison to a standard curve prepared by measuring IL-6 produced by stromal cells contacted with known concentrations of IL-1β. The bone marrow preparation can include, but is not limited to, a fresh supernatant from cultured bone marrow cells, a previously frozen supernatant from cultured bone marrow cells and a mononuclear cell preparation purified from bone marrow. The bone marrow preparation can be from, but is not limited to, a patient suffering from a MM or a multiple myeloma-related plasmaproliferative disorder.

In another embodiment, the invention features a method of detecting MM in an individual including culturing stromal cells with a bone marrow preparation from the individual, determining the amount of IL-6 produced by the stromal cell culture, wherein an elevated level of IL-6 is indicative of MM. The invention also features a method of identifying a patient with a multiple myeloma-related plasmaproliferative disorder likely to progress to active MM including the steps of culturing stromal cells with a bone marrow preparation from the patient, determining the amount of IL-6 produced by the stromal cell culture, wherein an elevated level of IL-6 is indicative of a likelihood the patient will progress to active MM. The multiple myeloma-related plasmaproliferative disorder can be, but is not limited to, MGUS or SMM. An elevated level of IL-6 can be, but is not limited to, a concentration of IL-6 greater than that produced by stromal cells incubated with 1 pg/ml of recombinant IL-1β. The bone marrow preparation can be, but is not limited to, a fresh supernatant from cultured bone marrow cells, a previously frozen supernatant from cultured bone marrow cells and a mononuclear cell preparation purified from bone marrow. An inhibitor of IL-1β can be added to the step of culturing the stromal cell culture with the bone marrow preparation. This inhibitor of IL-1β can be, but is not limited to, an anti-ILβ antibody, a soluble IL-1 receptor (sIL-1R) type I, a sIL-1R type II, an interleukin-1 receptor antagonist (IL-1ra) and an IL-1 TRAP.

The invention also features a method of monitoring the effectiveness of the treatment of a patient with a MM or a multiple myeloma-related plasmaproliferative disorder including culturing stromal cells with a bone marrow preparation from the patient after the initiation of treatment, determining the amount of IL-6 produced by the stromal cell culture and comparing the amount of IL-6 with a known standard or a patient determined standard.

In another embodiment, the invention features a method of identifying a patient with a multiple myeloma-related plasmaproliferative disorder likely to progress to active MM including culturing a bone marrow preparation from the patient with a T-cell line which produces IL-2 in response to IL-1β, determining the amount of IL-2 produced by the T-cell line, wherein an elevated level of IL-2 is indicative of a likelihood the patient will progress to active MM. The multiple myeloma-related plasmaproliferative disorder can be, but is not limited to, MGUS or SMM. The T-cell line can be, but is not limited to, EL4.6.1, LBRM 33 and primary cultures of thymocytes.

In another aspect, the invention features methods of treating patients by administering an inhibitor of IL-1β. This includes, but is not limited to, the treatment of patients with MM, MGUS, SMM and indolent multiple myeloma (IMM). It also includes administering an inhibitor IL-1β to patients in amounts effective to inhibit the production of IL-6 by patient bone marrow stromal cells or to inhibit myeloma cell proliferation. In another embodiment, the invention features methods of inhibiting the progression from MGUS or SMM to active MM by administering an inhibitor of IL-1β. The inhibitor of IL-1β used in these treatment methods can include, but is not limited to, an anti-ILβ antibody, a soluble receptor (sIL-1R) type I, a sIL-1R type II, an interleukin-1 receptor antagonist (IL-1 ra) or an IL-1 TRAP.

In another aspect, the invention features kits including an inhibitor of bioactive IL-1β, a negative control for the inhibitor of bioactive IL-1β and a positive control for bioactive IL-1β. In these kits the inhibitor of bioactive IL-1β can be, but is not limited to, an anti-ILβ antibody, a soluble IL-1 receptor (sIL-1R) type I, a sIL-1R type II, an interleukin-1 receptor antagonist (IL-1ra) or an IL-1 TRAP. The positive control for bioactive IL-1β can be, but is not limited to, recombinant IL-1β. The kits can include bone marrow stromal cells. The kits can also include a label or package insert indicating that the positive control for bioactive IL-1β can be used to prepare a standard curve of IL-6 produced by stromal cells contacted with known concentrations of bioactive IL-1β.

Unless otherwise defined, all technical and scientific terms used herein have the same meaning as commonly understood by one of ordinary skill in the art to which the invention belongs. Although methods and materials similar or equivalent to those described herein can be used in the practice and testing of the present invention, suitable methods and materials are described. All publications, patent applications, patents and other references mentioned herein are incorporated by reference in their entirety. In case of conflict, the present specification, including definitions, will control. In addition, the materials, methods, and examples are illustrative only and are not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6 shows the levels of IL-6 produced by stromal cells co-cultured with normal, MGUS, SMM and MM patient supernatants.

DETAILED DESCRIPTION

Figure 1:
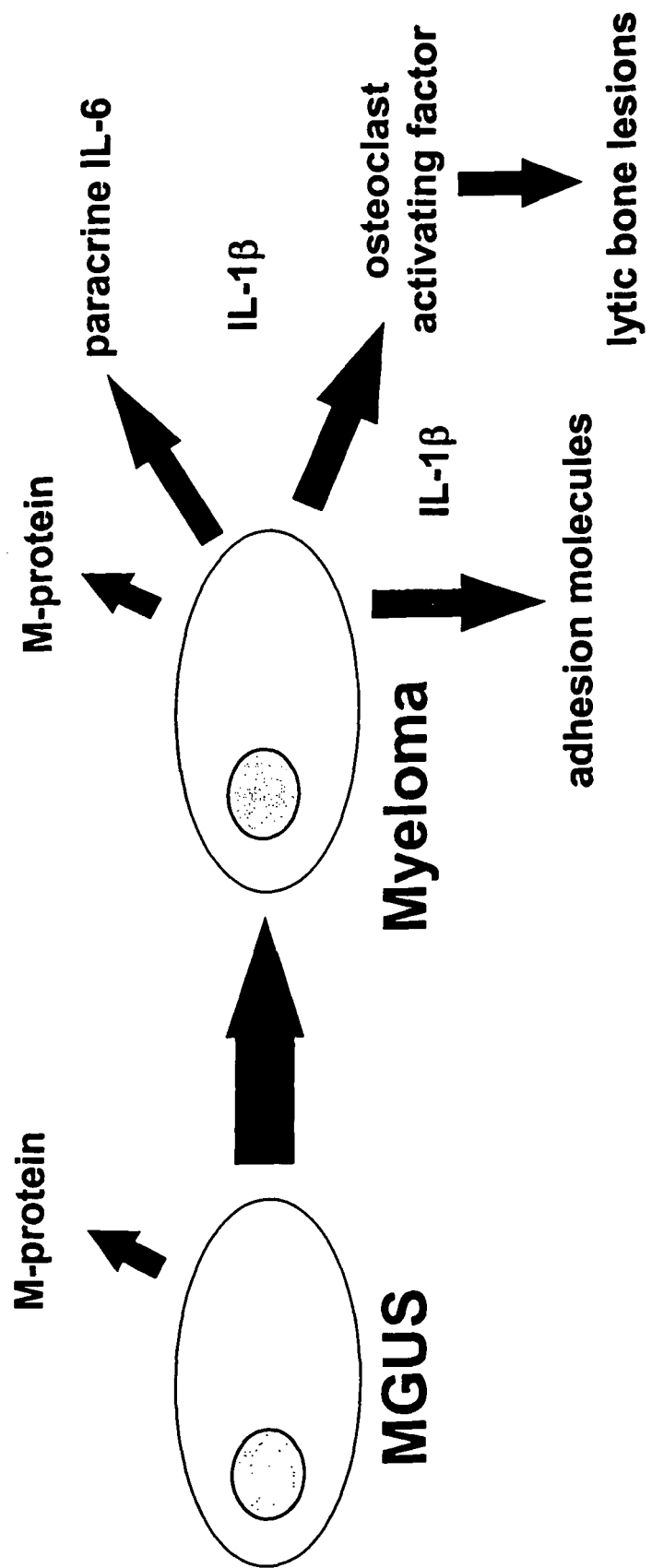
FIG. 1 is a schematic depicting the role of IL-1β expression in the progression of MGUS to MM.

The current invention is based on the observation that the biological effects of IL-1β closely parallel the clinical features of human myeloma. Interleukin-6 (IL-6) has been shown to be the central growth factor for myeloma cells and is produced by bone marrow stromal cells; See Kawano et al., (1988) *Nature* 332: 83; Schwab et al. (1991) *Blood* 77: 587; Klein et al. (1989) *Blood* 73: 517; and Portier et al. (1991) *Eur. J. Immunol.* 21: 1759. Although many cytokines can stimulate IL-6 production, IL-1β appears to be the major cytokine responsible for the paracrine production of IL-6 by marrow stromal cells in myeloma. See Carter et al. (1990) *Br. J. Haematol.* 74: 424. IL-1β is expressed by the plasma cells of virtually all myeloma patients; however, it is not produced by normal plasma cells. See Lust and Donovan (1999) *Hematology-Oncology Clinics of North America* 13: 1117; Donovan et al. (1998) *Leukemia* 12: 593; and Lacy et al. (1999) *Blood* 93: 300.

The current invention is based on the observation that aberrant IL-1β produced by myeloma cells is able to induce IL-6 production by bone marrow stromal cells and the IL-6 stimulates myeloma cells to grow. This paracrine model of IL-6 production suggests a therapeutic approach for the treatment of myeloma: inhibition of IL-1β induced IL-6 production with an IL-1β inhibitor. Such treatment with an IL-1 inhibitor will reduce plasma cell growth and slow or reverse further progression of the disease.

As shown in Table 1, specific criteria exist that serve as useful guidelines to allow clinicians to differentiate between MM and other multiple myeloma-related plasma proliferative disorders. Multiple myeloma-related plasmaproliferative disorders are defined to include MGUS, smoldering MM (SMM) and indolent MM (IMM). Patients with MGUS, a clinically benign condition, usually have less than 10% marrow plasma cells, a serum monoclonal protein <3 gm/dL, no urinary Bence Jones protein and no anemia, renal failure, lytic bone lesions, or hypercalcemia. In contrast, patients with active MM present with a marrow plasmacytosis of ≧10%, a serum monoclonal protein of ≧3 gm/dL, a 24-hour urine monoclonal protein of ≧1 gm, and lytic bone lesions. MM patients also often present with back pain, severe fatigue, pneumonia, or bone pain. Kyle and Lust (1989) *Seminars in Hematology* 26: 176. Patients with SMM are usually asymptomatic. They have a marrow plasmacytosis of ≧10% and/or a serum monoclonal protein of ≧3 gm/dL. Lytic bone lesions are absent and they have stable disease. See Kyle and Greipp (1980) *N. Engl. J. Med.* 302: 1347. Patients with IMM are similar to those with SMM, except bone lesions may be present on bone survey studies. In contrast to MM patients, who all receive chemotherapy, patients with MGUS, SMM and IMM have stable disease and are followed off chemotherapy. However, patients who have a serum monoclonal protein of >2.0 g/dL are at high risk of eventually developing active MM, requiring chemotherapy. Such patients are candidates for novel therapeutic strategies to inhibit or prevent the development of active MM.

TABLE 1

| Characteristic | MM | SMM | MGUS |
|---|---|---|---|
| Marrow plasma cells | ≧10% | ≧10% | <10% |
| Serum M-spike | ≧3 g/dL | ≧3 g/dL | <3 g/dL |
| Bence Jones Protein | ≧1 g/24 h | <1 g/24 h | <1 g/24 h |
| Anemia | Usually Present | May be Present | Absent |
| Hypercalcemia, Renal Insufficiency | May be Present | Absent | Absent |
| Lytic bone lesions | Usually Present | Absent | Absent |

During long-term follow-up of 241 patients with MGUS, 59 patients (24.5%) went on to develop MM or a related disorder. See Kyle (1993) *Mayo Clinic Proc.* 68: 26-36. Closer examination of the individuals that progressed to MM revealed that the majority of these patients remained stable for an extended period of time and then subsequently progressed to overt MM over a relatively short period of time. Of the 59 patients that progressed, 39 went on to develop MM. Of these 39 patients, 18 had serial serum studies performed. In these eighteen patients, the M-protein remained stable for a median of 8 years and then increased slowly over 1-4 years in 11 patients or rapidly in less than 1 year in seven patients.

As summarized in Table 2, supernatants of bone marrow cells from normal individuals stimulated the production of minimal amounts of IL-6 by marrow stromal cells. Supernatants from MGUS patients generated low, but detectable, amounts of IL-6, slightly above normal individuals. All myeloma patients studied produced IL-6 levels above normal individuals and some were 100-200 fold elevated. The SMM patients appeared to fall into two groups: those with high IL-6 values (4 patients) and those with low values (10 patients). Two of the four patients with high values of Il-1 β induced IL-6 production have subsequently progressed to active myeloma within two years. Thus, up regulation of IL-1β production appears critical in the progression from MGUS or SMM to active MM. See FIG. 1.

TABLE 2

IL-6 Production From Stromal Cell Co-cultures

| Diagnosis | Number | Average IL-6 (pg/ml) | IL-6 Range (pg/ml) |
|---|---|---|---|
| Normal | 2 | 114 | 110–117 |
| MGUS | 5 | 426 | 114–1258 |
| SMM | 10 | 1711 | 154–3474 |
| SMM | 4 | 23198 | 6987–35000 |
| MM | 10 | 10775 | 610–27297 |

The invention features an assay for bioactive IL-1β that allows for the quantitative detection of functional, bioactive IL-1β in supernatants of bone marrow cells taken from patients with plasmaproliferative disorders. As shown in FIGS. 3-6, studies on bone marrow cells from patients with MGUS, SMM and active MM indicate that this assay will be useful as a biomarker in differentiating those patients with stable MGUS/SMM from those progressing to active MM.

IL-1β

Interleukin-1 (IL-1) is produced predominantly by peripheral blood monocytes during an inflammatory response and exists in two distinct forms, IL-1α and IL-1β. For a review, see Dinarello (1996) *Blood* 87: 2095. IL-1β is synthesized as a biologically inactive precursor, proIL-1β, which lacks a conventional leader sequence and is not processed by a signal peptidase. See March (1985) *Nature* 315: 641. proIL-1β is cleaved by an intracellular cysteine protease between Asp-116 and Ala-117 to produce the biologically active C-terminal fragment found in human serum and synovial fluid. See Sleath et al. (1992) *J. Biol. Chem.* 265: 14526 and Howard et al. (1991) *J. Immunol.* 147: 2964. Bioactive IL-1β includes, but is not limited to, the biologically active C-terminal fragment of IL-1β after cleavage between Asp-116 and Ala-117.

Assays for Bioactive IL-1β

This invention provides methods of detecting patients with MM and for identifying patients likely to transform from multiple myeloma-related plasmaproliferative disorders, such as MGUS or SMM, to active MM. Also included are methods of monitoring the effectiveness of the treatment of a patient with MM or a multiple myeloma-related plasmaproliferative disorder comprising quantitating levels of bioactive IL-1β produced by patient bone marrow plasma cells at various time points in treatment. These time points include, but are not limited to, prior to the start of treatment and anytime point after treatment has commenced. Such methods involve the quantitation of bioactive IL-1β produced by bone marrow plasma cells. Any art known assay for the quantitation of bioactive IL-1β is included within the scope of the invention. Such assays include, but are not limited to, osteoclast activation assays, T-cell assays and stromal cell assays.

T-Cell Bioassay

As outlined in *Cytokines: A Practical Approach*, ed. F. R. Blackwill, Oxford University Press (1991) pp. 311-12, bioassays for functional IL-1 can utilize the ability of IL-1β to induce IL-2 production by T-cell lines, such as EL4.6.1 and LBRM 33, or by primary cultures of thymocytes (LAF assay). Alternatively, IL-1 can be assayed by measuring its ability to stimulate the proliferation of lines such as the subclone D10S of the murine T-helper cell-line D10.64.1. A subclone, NOB-1, of the murine thymoma cell-line EL4.6.1 provides a simple and sensitive bioassay for IL-1. This line produces IL-2 in response to IL-1, which is measured using the CTLL-2 assay. See *Cytokines: A Practical Approach*, ed. F. R. Blackwill, Oxford University Press (1991) pp. 311-312.

Stromal Cell Bioassay for IL-6

Figure 2:
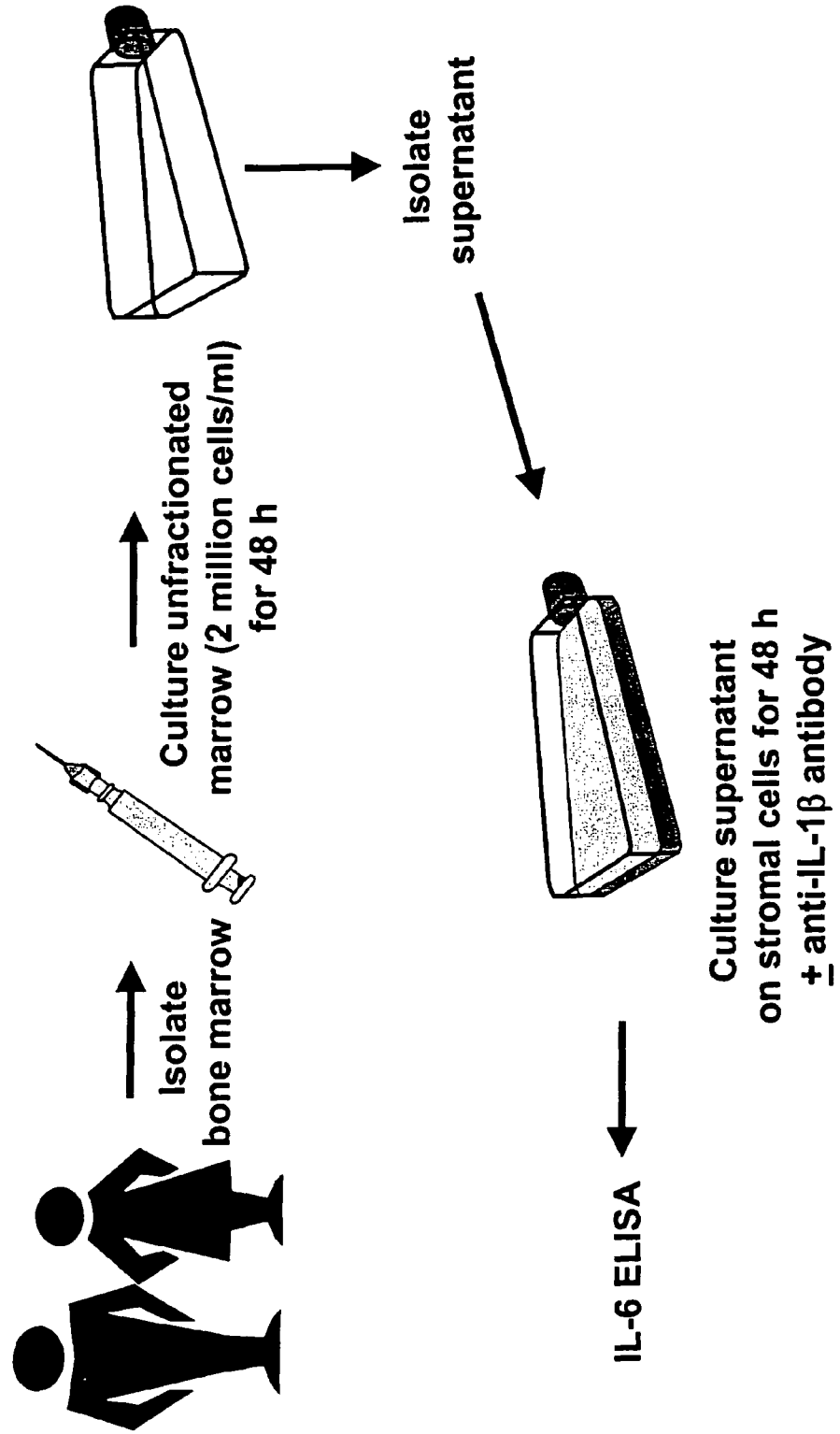
FIG. 2 is a schematic representation of the bioassay for IL-1β induced IL-6 production.

The stromal cell bioassay for IL-1β quantitates the amount of IL-6 produced by stromal cells cultured with bone marrow preparations from patients with various plasmaproliferative disorders. The assay is diagramed in FIG. 2. The assay comprises culturing bone marrow stromal cells with patient bone marrow preparations and determining the amount of IL-6 produced by the stromal cells. The amount of IL-6 produced is then correlated to the concentration of IL-1β in the bone marrow preparation by comparison to a standard curve prepared by measuring IL-6 produced by stromal cells contacted with known concentrations of IL-1β.

Normal bone marrow stromal cells can be obtained commercially, for example, from Clonetics, Walkersville, Md. Bone marrow preparations include, but are not limited to, fresh supernatants from patient bone marrow cells, previously frozen supernatants from patient bone marrow cells and fresh mononuclear cell preparations of patient bone marrow cells. It can be technically difficult to have marrow stromal cells constantly available when patient bone marrow samples are drawn. Thus, it is often convenient to culture bone marrow cells, collect the supernatants and store the supernatants at −80° C. until stromal cells are available. However, when stromal cell cultures are available, patient bone marrow cells can be plated directly onto stromal cells. Stromal cells are cultured with either IL-1β standards or patient supernatants, with or without the addition of an anti-IL-1β antibody or other IL-1β inhibitor. Recombinant IL-1β, obtained commercially, for example, from R&D Systems, Inc., Minneapolis, Minn., at concentrations including, but not limited to, 0.1 pg/ml, 1.0 pg/ml, 10 pg/ml, 100 pg/ml and 1000 pg/ml can be used to prepare a standard curve of IL-6 produced by stromal cells contacted with known concentrations of IL-1β.

Stromal cell supernatants are analyzed for IL-6 concentrations using any art known assay for the quantitation of IL-6. One such assay is the human IL-6 ELISA kit from BioSource International, Inc., Camarillo, Calif. (Catalog Numbers KHC0061, KHC0062, KHC0063 or KHC0064). All such assays for the quantitation of IL-6 are performed according to the manufacturer's specifications. An elevated level of IL-6 can be, for example, a concentration of IL-6 greater than that produced by stromal cells incubated with a standard concentration of recombinant IL-1β, such as, for example, 0.1 pg/ml, 1 pg/ml or 10 pg/ml recombinant IL-1β. An elevated level of IL-6 can also be, for example, a concentration of IL-6 greater than that produced by stromal cells from normal, healthy individuals. Alternatively, an elevated level of IL-6 can also be determined by a patient specific standard; for example, an IL-6 concentration is elevated if it is greater than the IL-6 concentration produced by stromal cells obtained from the same patient at an earlier or later point in time.

Therapeutic Methods

This invention provides methods for the treatment of patients with MM comprising the administration of inhibitors of IL-1β. The invention also provides methods of chemoprevention, i.e., preventing the transition from MGUS or SMM to MM comprising the administration of inhibitors of IL-1β.

Inhibitors of IL-1β

Inhibitors of bioactive IL-1β include, but are not limited to, antibodies that bind to IL-1β, antibodies that bind to the IL-1 receptor or to peptide fragments of the receptor, the IL-1 receptor antagonist protein (IL-1ra), soluble IL-1 receptor (sIL-1R), peptide fragments of the IL-1 receptor, and chimeric molecules such as IL-1 TRAP.

Antibodies to IL-1β

Antibodies having specific binding affinity for IL-1β can be produced through standard methods. Alternatively, antibodies may be commercially available, for example, from R&D Systems, Inc., Minneapolis, Minn. The terms "antibody" and "antibodies" include polyclonal antibodies, monoclonal antibodies, humanized or chimeric antibodies, single chain Fv antibody fragments, Fab fragments, and F(ab)₂ fragments. Polyclonal antibodies are heterogeneous populations of antibody molecules that are specific for a particular antigen, which are contained in the sera of the immunized animals. Polyclonal antibodies are produced using well-known methods.

Monoclonal antibodies, which are homogeneous populations of antibodies to a particular epitope contained within an antigen, can be prepared using standard hybridoma technology. In particular, monoclonal antibodies can be obtained by any technique that provides for the production of antibody molecules by continuous cell lines in culture such as described by Kohler, G. et al., *Nature,* 1975, 256: 495, the human B-cell hybridoma technique (Kosbor et al., *Immunology Today,* 1983, 4: 72; Cole et al., *Proc. Natl. Acad. Sci. USA,* 1983, 80: 2026), and the EBV-hybridoma technique (Cole et al., "Monoclonal Antibodies and Cancer Therapy", Alan R. Liss, Inc., 1983, pp. 77-96). Such antibodies can be of any immunoglobulin class including IgG, IgM, IgE, IgA, IgD, and any subclass thereof. The hybridoma producing the monoclonal antibodies of the invention can be cultivated in vitro or in vivo.

A chimeric antibody is a molecule in which different portions are derived from different animal species, such as those having a variable region derived from a murine monoclonal antibody and a human immunoglobulin constant region. Chimeric antibodies can be produced through standard techniques.

Antibody fragments that have specific binding affinity for IL-1β can be generated by known techniques. For example, such fragments include, but are not limited to, F(ab')₂ fragments that can be produced by pepsin digestion of the antibody molecule, and Fab fragments that can be generated by reducing the disulfide bridges of F(ab')₂ fragments. Alternatively, Fab expression libraries can be constructed. See, for example, Huse et al., 1989, *Science,* 246: 1275. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques. See, for example, U.S. Pat. No. 4,946,778.

IL-1ra

The IL-1 receptor antagonist (IL-1 ra) (also called IRAP, for IL-1 receptor antagonist protein) is a third member of the IL-1 family. It acts as a natural antagonist of IL-1α and IL-1β by binding to the IL-1 receptor but not transducing an intracellular signal or a biological response. The gene encoding this antagonist of IL-1 has been described. See Hannum et al. (1990) *Nature* 343: 336-340; Eisenberg et al. (1990) *Nature* 343: 341-346; and Carter et al. (1990) *Nature* 344: 633-638. IL-1ra inhibits the biological activities of IL-1 both in vitro and in vivo, and has been shown to be effective in animal models of septic shock, rheumatoid arthritis, graft versus host disease, stroke, cardiac ischemia; it is currently in clinical trials for some of these indications. For a review, see Dinarello and Thompson (1991) *Immunol. Today* 12: 404-410. In vivo administration of IL-1ra is well tolerated. Normal animals, including humans, can be infused intravenously with high doses of this protein without any change in physiological or metabolic parameters. For example, human volunteers infused with 133 mg/h IL-1ra for 72 hours exhibited no change in clinical or laboratory values. See Dinarello et al. (1993) *J. Amer. Med. Assoc.* 269: 1829-1835.

sIL-1R

There are three known IL-1 receptor subunits. The active receptor complex consists of the type I receptor and IL1RAcP (for IL-1 receptor accessory protein). The type I receptor is responsible for binding of the three naturally occurring ligands (IL-1α, IL-1β and IL-1ra) and is able to do so in the absence of the IL1RAcP. However, signal transduction requires interaction of IL-1α or IL-1β with the IL1RAcP. IL-1ra does not interact with the IL-1RAcP and hence cannot signal. A third receptor subunit, the type II receptor, binds IL-1α or IL-1β, but cannot signal due to its lack of an intracellular domain. Rather it acts as a decoy either in its membrane form or as an antagonist in a cleaved secreted form, thus inhibiting IL-1 activity. For a review, see Dinarello (1996) *Blood*, 87: 2095-2147.

Also included as inhibitors of bioactive IL-1β are peptides corresponding to portions of the IL-1 receptor. These include, but are not limited to, synthetic peptides corresponding to residues 86-93 of the human type I IL-1 receptor, which bind IL-1 (α and β) and inhibit IL-1 activity in vitro and in vivo. See Tanihara et al. (1992) *Biochem. Biophys. Res. Commun.* 188: 912.

IL-1 TRAP

The IL-1 TRAP is as essentially described in U.S. Pat. No. 5,844,099. Briefly, the IL-1 TRAP is a fusion protein comprising the human cytokine receptor extracellular domains and the Fc portion of human IgG1. The IL-1 TRAP incorporates into a single molecule the extracellular domains of both receptor components required for IL-1 signaling; the IL-1 Type I receptor (IL-1RI) and the IL-1 receptor accessory protein (AcP). Since it contains both receptor components, the IL-1 TRAP binds IL-1β and IL-1α with picomolar affinity, while the IL-1RI alone in the absence of AcP binds with ~1 nM affinity. The IL-1 TRAP was created by fusing the sequences encoding the extracellular domains of the AcP, IL-1RI, and Fc inline without any intervening linker sequences. An expression construct encoding the fusion protein is transfected into Chinese hamster ovary (CHO) cells, and high producing lines are isolated that secrete the IL-1 TRAP into the medium. The IL-1 TRAP is a dimeric glycoprotein with a protein molecular weight of 201 kDa and including glycosylation has a total molecular weight of ~252 kDa. The dimer is covalently linked by disulfide bonds in the Fc region.

Rheumatoid arthritis is a chronic autoimmune disease in which the immune system attacks the tissue that lines and cushions the joints. Excess IL-1β production mediates the cartilage and joint damage associated with rheumatoid arthritis. In preclinical trials, the IL-1 TRAP was a potent blocker of IL-1 activity, has a long half-life in the blood, penetrates into the joints and blocks IL-1-induced cartilage erosion in animal models. A placebo controlled, double blind, dose-escalation Phase I trial is currently underway to assess the safety and tolerability of the IL-1 TRAP for the treatment of rheumatoid arthritis. See http://regeneron.com.

Pharmaceutical Compositions

Effective doses of an IL-1β inhibitor useful for treating MM and multiple myeloma-related plasmaproliferative disorders may be determined using methods well known in the art. See for example Fingle et al., *The Pharmaceutical Basis of Therapeutics*, Goodman and Gilman, eds. MacMillan Publishing Co., New York, pp. 1-46 (1975) or "Remington's Pharmaceutical Science." Pharmaceutical compositions for use according to the current invention include the IL-1β inhibitor in a pharmaceutically acceptable liquid (including, but not limited to sterile water, phosphate buffered saline or dextrose solution), solid (e.g. wax) or semi-solid carrier (e.g. gelfoam), incorporated into liposomes, microcapsules or controlled release preparations (including inhibitor expressing cells). The administration route may be any mode of administration known in the art, including, but not limited to, intravenously, intrathecally, subcutaneously, by injection into involved tissue, intraarterially, intranasally, orally, or via an implanted device. Pharmaceutical compositions of this invention comprise any of the compounds of the present invention, and pharmaceutically acceptable salts thereof, with any pharmaceutically acceptable carrier, adjuvant or vehicle.

A therapeutically effective amount is an amount capable of producing a medically desirable result in a treated mammal, e.g., a human patient. The dosage range required depends on the individual IL-1β inhibitor selected, the route of administration, the nature of the formulation, the nature of the subject's condition, and the judgment of the attending practitioner. Wide variations in the needed dosage are to be expected in view of the variety of compounds available and the differing efficiencies of various routes of administration. For example, oral administration would be expected to require higher dosages than administration by intravenous injection. Dosages will vary, but preferred dosage for administration is from approximately 0.01 to 1,000 mg/kg of body weight. For example, a preferred dosage can be, but is not limited to, 0.01, 0.05, 0.1, 0.5, 1.0, 5.0, 10, 25, 50, 100, 500, 750 or 1,000 mg/kg of body weight. Variations in these dosage levels can be adjusted using standard empirical routines for optimization, as is well understood in the art. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

Typically, the pharmaceutical compositions of this invention will be administered from about 1 to 5 times per day or, alternatively, as a continuous infusion. Such administration can be used as a chronic or acute therapy. The amount of active ingredient that may be combined with the carrier materials to produce a single dosage form will vary depending upon the host treated and the particular-mode of administration. A typical preparation will contain from about 5% to about 95% active compound (w/w). Preferably, such preparations contain from about 20% to about 80% active compound.

The IL-1β inhibitors of the present invention may be employed alone or in conjunction with other therapeutic agents. Such therapeutic agents may include, but are not limited to, additional IL-1β inhibitors, chemotherapy agents and analgesics. Such agents may be administered prior to, sequential to or concurrent with the administration of the IL-1β inhibitor to the patient.

Kits and Articles of Manufacture

In further embodiments, the present invention includes kits or articles of manufacture for conveniently and effectively carrying out the methods in accordance with the present invention.

Inhibitors of IL-1β can be packaged as kits or articles of manufacture that contain one or more unit dosage forms. Each kit or article of manufacture typically comprises at least one container with a label. This container may, for example, comprise glass or plastic bottles or vials or metal or plastic foil. Another example of such a kit is a "blister pack." Blister packs are well known in the packaging industry and are widely used for packaging pharmaceutical unit dosage forms. The package may also be accompanied by a label or packaging insert giving instructions for the intended use of the enclosed IL-1β inhibitor, for example, indicating that the inhibitor may be administered for the treatment of plasmaproliferative disorders, such as MM, MGUS or SMM. These directions may indicate that the IL-1β inhibitor may be used alone or in combination with other agents. The package may also include these other agents. The package may also include materials desirable from a commercial or user standpoint, including buffers, filters, needles, syringes.

The scope of the invention also includes kits containing materials necessary for the determination of the concentration of IL-1β present in bone marrow preparations and other supernatants. These kits comprise a positive control for bioactive IL-1β and an inhibitor of bioactive IL-1β. The kits may further comprise a negative control for the inhibitor of bioactive IL-1β. This negative control may be, but is not limited to, VEGF TRAP. The VEGF TRAP is a fusion protein comprising the receptor for vascular endothelial growth factor (VEFGF) and portions of human IgG, prepared as essentially described in U.S. Pat. No. 5,844,099. See also, http://regeneron.com. The kits may further comprise bone marrow stromal cells. The positive control for bioactive IL-1β may be, but is not limited to, recombinant IL-1β. The inhibitor of bioactive IL-1β may be, but is not limited to an anti-IL-1β antibody, a soluble IL-1 receptor (sIL-1R) type I, a sIL-1R type II, an interleukin-1 receptor antagonist (IL-1ra) or IL-1 TRAP. The kit may include a label or packaging insert indicating that the positive control for bioactive IL-1β may be used to prepare a standard curve of IL-6 produced by stromal cells contacted with known concentrations of bioactive IL-1β.

EXAMPLES

Example 1

Figure 3:
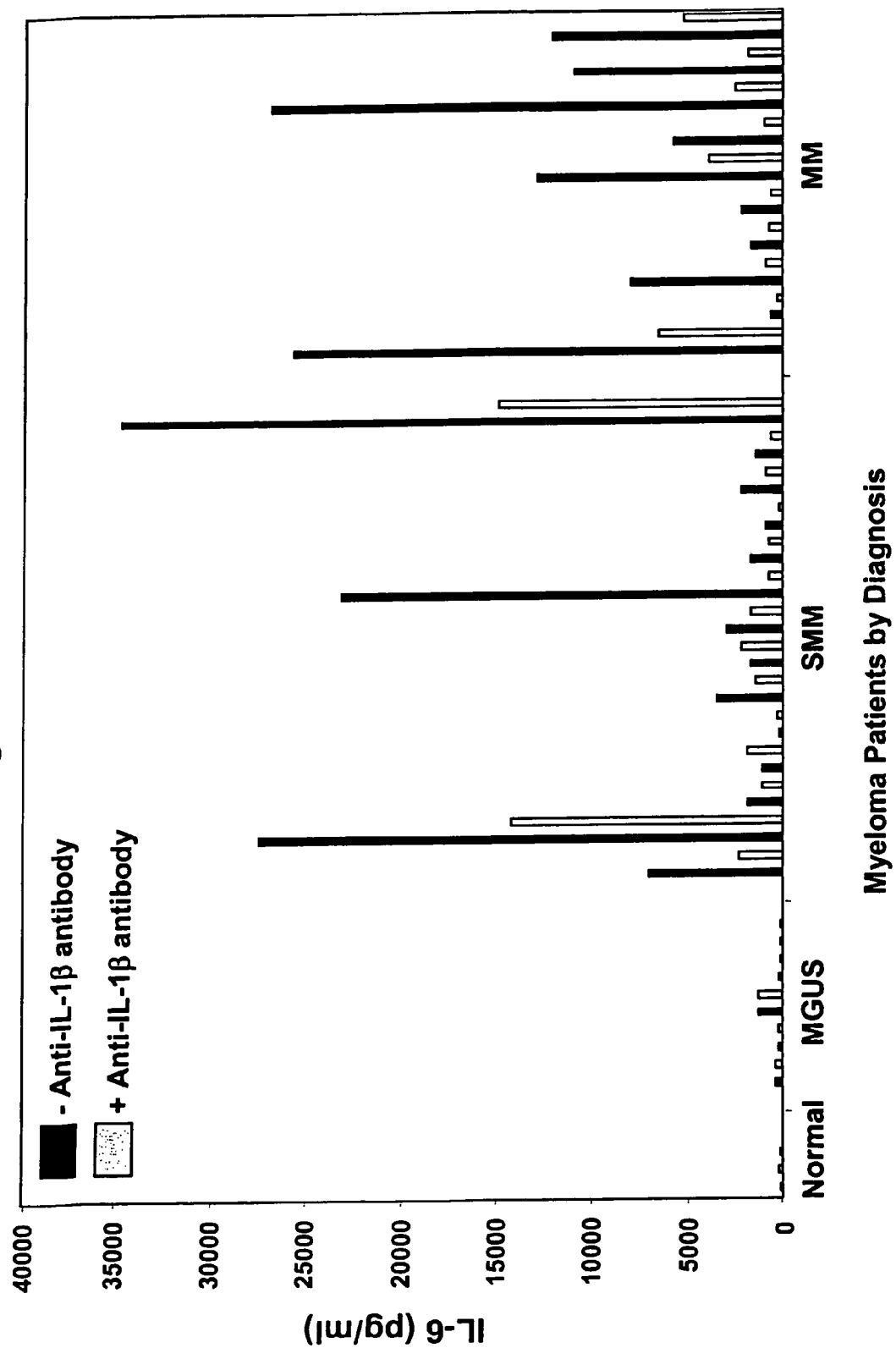
FIG. 3 shows levels of IL-1β induced IL-6 production in MGUS, SMM and MM patients. An anti-IL-1β antibody is used as an inhibitor of IL-1β bioactivity.

IL-6 produced by stromal cells cultured with patient bone marrow cells with the addition of an anti-IL-1β antibody as an inhibitor of bioactive IL-1β: Ficoll purified bone marrow cells from patients with various plasmaproliferative disorders were cultured at 2×10$^6$ cells/ml for 48 hours. Supernatants were frozen at −80° C. until assayed on stromal cells. Normal stromal cells (Clontech, Walkersville, Md.) were plated at 1×10$^5$ cells/ml and incubated at 37° C. for 48 hours. After 48 hours, the stromal cells were washed and incubated with patient supernatants, with or without a polyclonal neutralizing anti-IL-1β antibody. Cultures were incubated at 37° C. for an additional 48 hours. Supernatants were harvested and frozen at −20° C. until analysis of IL-6 production. Supernatants were analyzed for IL-6 using a human IL-6 ELISA kit (BioSource International, Inc., Camarillo, Calif.) according to the manufacturer's specifications. Results are shown in FIG. 3.

Example 2

Figure 4:
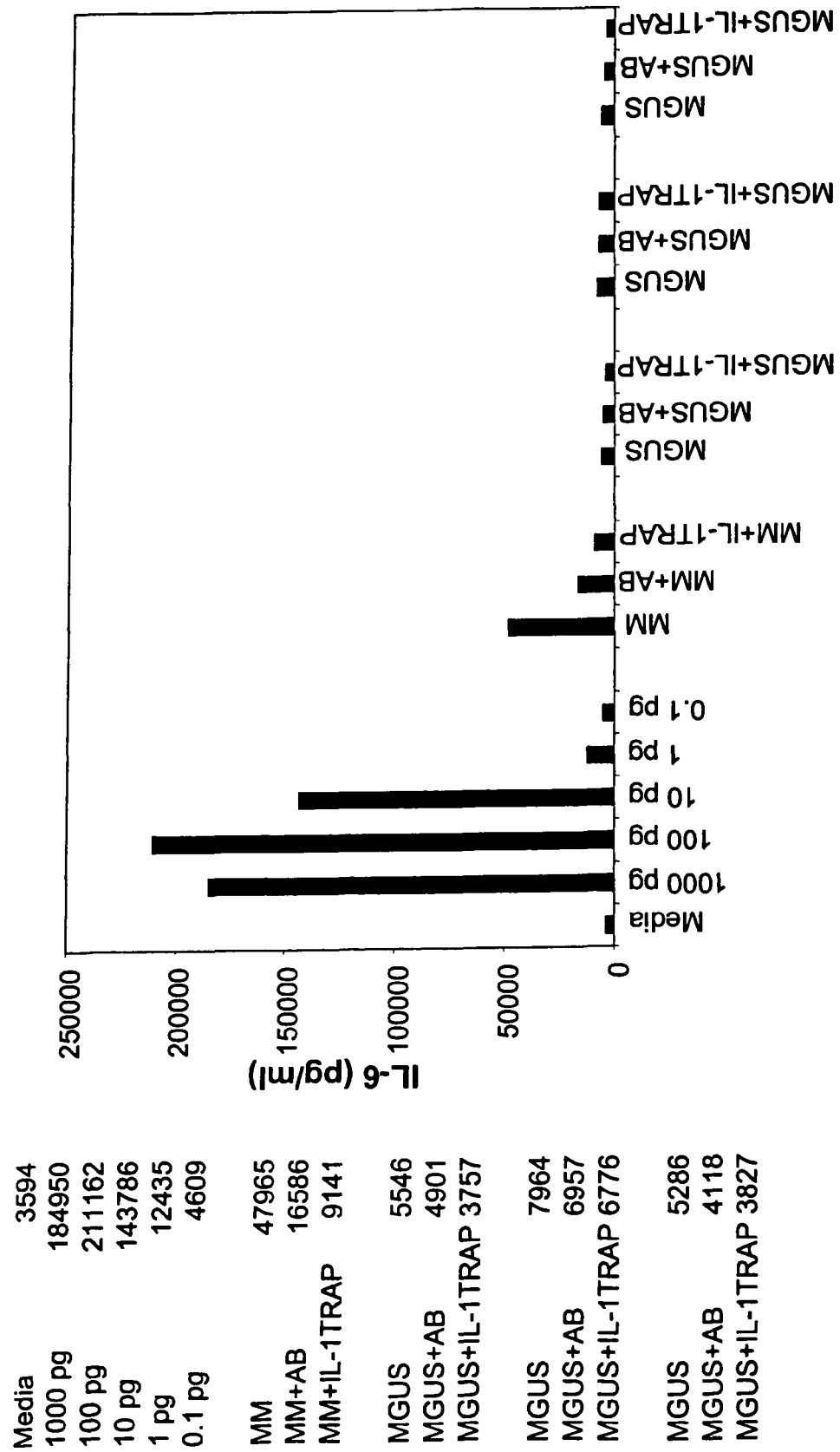
FIG. 4 shows levels of IL-1β induced IL-6 production in MGUS and MM patients. Both an anti-IL-1β antibody and IL-1 TRAP are used as inhibitors of IL-1β bioactivity.

IL-6 produced by stromal cells cultured with patient bone marrow cells with the addition of an IL-1 TRAP as an inhibitor of bioactive IL-1β: Ficoll purified bone marrow cells from patients with various plasmaproliferative disorders were cultured at 2×10$^6$ cells/ml for 48 hours. Supernatants were frozen at −80° C. until assayed on stromal cells. Normal stromal cells (Clontech, Walkersville, Md.) were plated at 1×10$^5$ cells/ml and incubated at 37° C. for 48 hours. After 48 hours, the stromal cells were washed and incubated with either IL-1β standards or patient supernatants, with or without IL-1 TRAP as an inhibitor of bioactive IL-1β. Cultures were incubated at 37° C. for an additional 48 hours. Supernatants were harvested and frozen at −20° C. until analysis of IL-6 production. Supernatants were analyzed for IL-6 using a human Il-6 ELISA kit (BioSource International; Inc., Camarillo, Calif.) according to the manufacturer's specifications. To prepare a standard curve of IL-6 produced by known concentrations of IL-1β, bone marrow stromal cells were incubated with media or recombinant IL-1β in the following concentrations; 1000, 100, 10, 1.0 or 0.1 pg/ml. Results are shown in FIG. 4.

Example 3

Figure 5A:
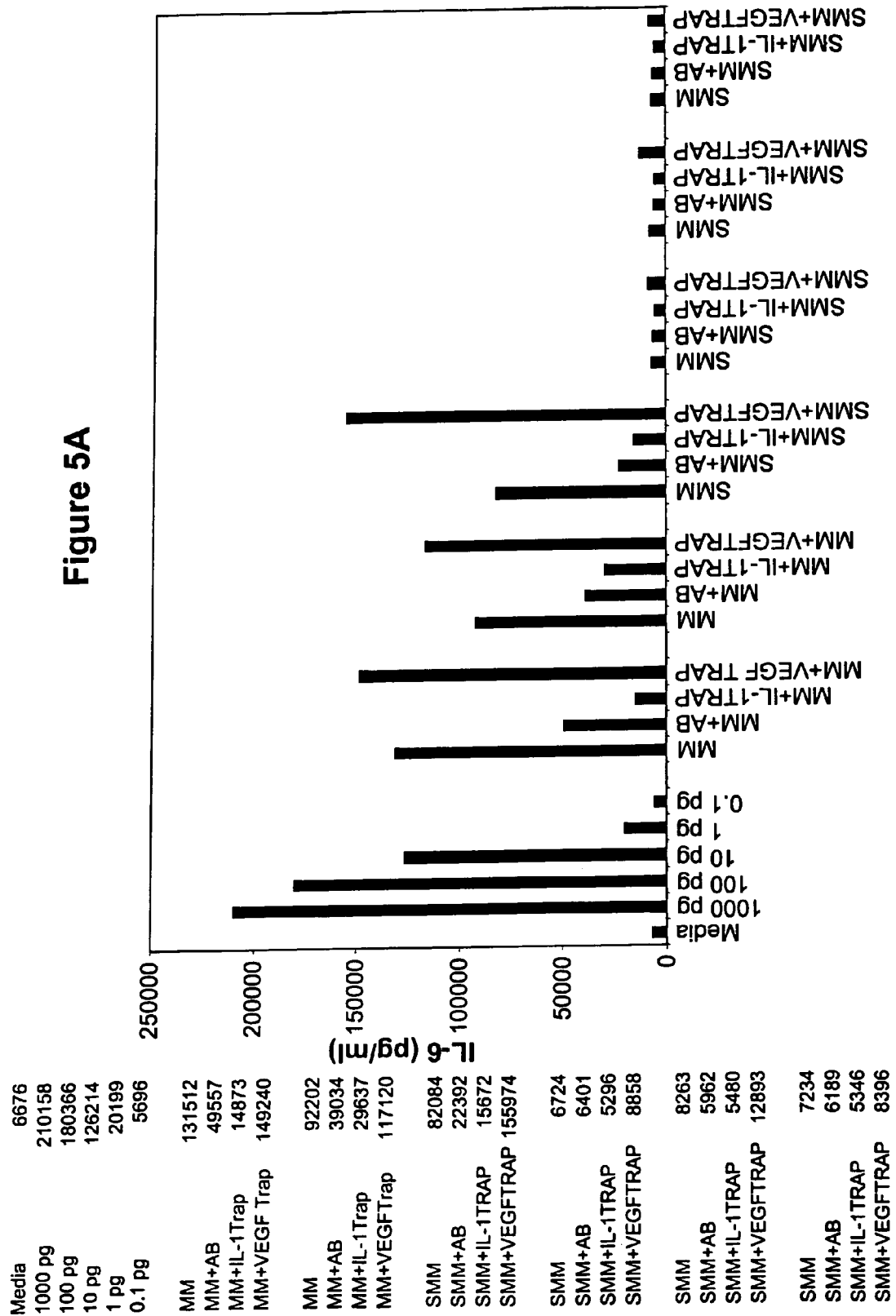
FIGS. 5A and 5B show levels of IL-1β induced IL-6 production in MGUS, SMM and MM patients. Both an anti-IL-1β antibody and IL-1 TRAP are used as inhibitors of IL-1β bioactivity. VEGFTRAP is used as a negative control.
Figure 5B:
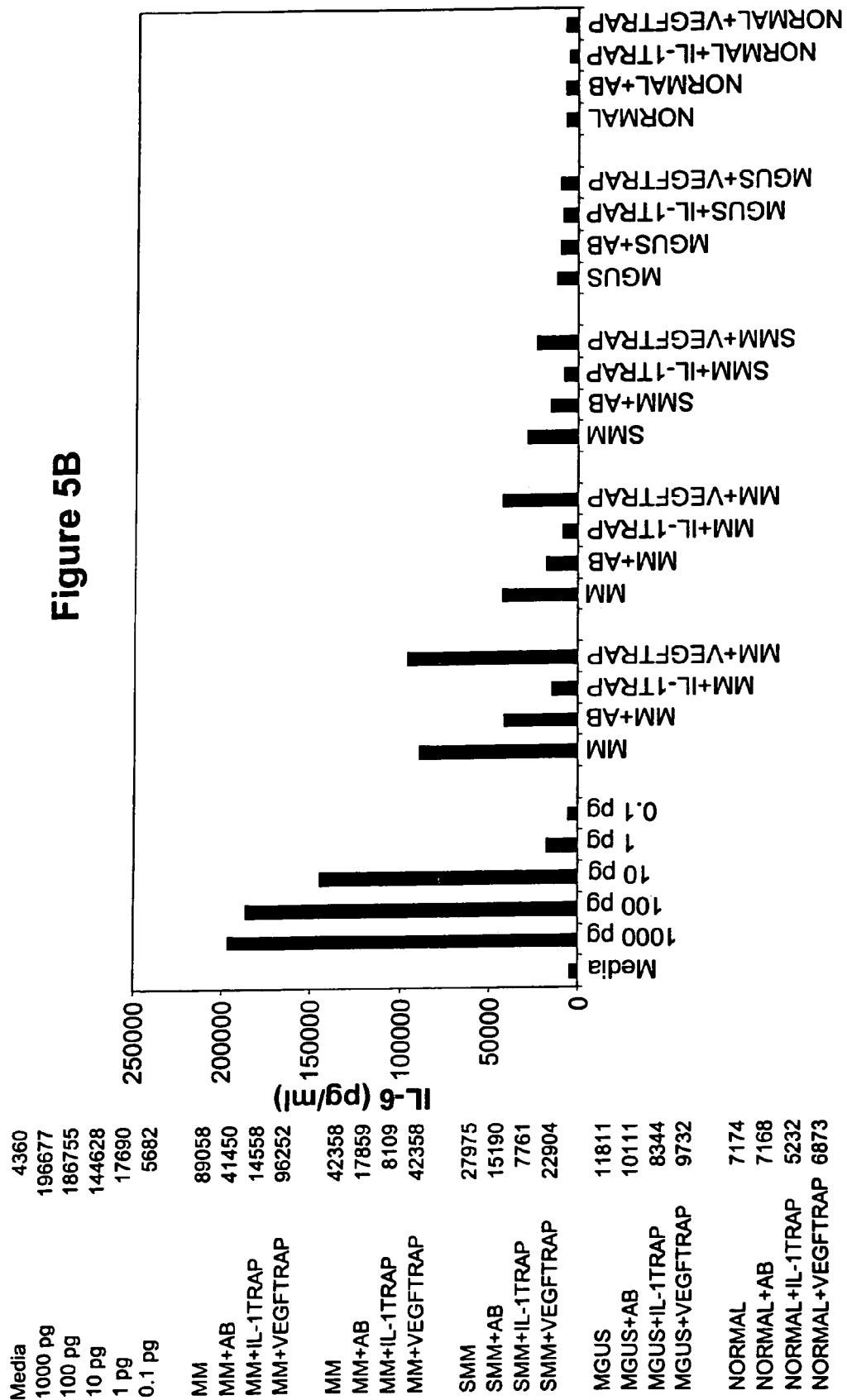

IL-6 produced by stromal cells cultured with patient bone marrow cells with the addition of an Anti-IL-11 antibody, an IL-1 TRAP or a VEGF TRAP: IL-6 produced by stromal cells cultured with bone marrow cells from patients with various plasma proliferative diseases with the addition of an anti-IL-1β polyclonal antibody, an IL-1 TRAP or a VEGF TRAP are shown in FIGS. 5A and 5B. The assay was performed as outlined in Examples 1 and 2, above. Patient supernatants were assayed in a total volume of 0.5 ml as follows:

0.5 ml patient supernatant+media alone
0.5 ml patient supernatant+10 micrograms/well anti-IL-1 antibody
0.5 ml patient supernatant+1 microgram/well IL-1 TRAP
0.5 ml patient supernatant+1 microgram/well VEGF TRAP The supernatants were harvested and an IL-6 ELISA was performed. As shown in FIG. 5B, supernatants from normal patients or those with MGUS induce only small amounts of IL-6. In contrast, as shown in FIGS. 5a and 5B, patients with MM induce IL-6 levels equivalent to 1-10 pg of IL-1β. Some SMM patients may generate IL-6 levels similar to normal/MGUS patients while others may induce IL-6 levels similar to patients with MM. SMM patients with high levels of IL-6 induction have been observed to progress to active MM in 1-2 yrs requiring chemotherapy. The IL-1 TRAP was superior to the anti-IL-1β antibody at inhibiting IL-6 production by patient supernatants especially in view of the fact that 10 fold more antibody was utilized. The IL-1 TRAP was very effective at inhibiting IL-6 production in all patients with MM or SMM that had elevated IL-6 levels. For example, the first MM patient shown in FIG. 5A produced 131,512 pg/ml of IL-6 that was inhibited to 14,873 pg/ml by the addition of IL-1 TRAP, a reduction of 93% compared to the media control. The VEGF TRAP caused no reduction in IL-6 production and may have slightly stimulated IL-6 production in certain cases. The first SMM patient shown on FIG. 5A indicate an IL-6 level of 82,084 pg/ml, which was reduced to 15,672 pg/ml with the addition of an IL-1 TRAP (a 88% reduction). This individual is likely to progress to active MM based on the high IL-6 level generated by the patient supernatant. In vitro results demonstrating a significant reduction in IL-6 levels with the addition of the IL-1 TRAP indicate that this patient may benefit from therapy with a potent IL-1 inhibitor, such as the IL-1 TRAP.

Example 4

IL-6 produced by stromal cells cultured with bone marrow cells from a variety of patients: FIG. 6 is a summary of the level of IL-6 produced by bone marrow cells from a collection of patients with MM, MGUS and SMM. The same assay system outlined in Examples 1 and 2 was used. Supernatants of bone marrow cells from normal individuals stimulated the production of minimal amounts of IL-6 by marrow stromal cells. Therefore, purification of myeloma cells from patient marrows was not necessary. Supernatants from MGUS patients generated low but detectable amounts of IL-6 slightly above normal individuals. All MM patients studied produced IL-6 levels above normal individuals and some were 100-200 fold elevated. All patients with MM had bone lesions evident on X-ray. Interestingly, one MM patient with an IL-6 value of 25,962 had a labeling index of 1.4% and a second MM patient with an IL-6 value of 27,297 had a labeling index of 5%. The SMM patients appeared to fall into two groups: those with high values of IL-6 production (4 patients) and those with low values of IL-6 production (10 patients). Two of the four patients with high values of IL-6 production have subsequently progressed to active myeloma within two years. These results indicate that IL-1β induced IL-6 production is a useful criteria for differentiating those patients that will progress from MGUS/SMM to active MM.

Other Embodiments

It is to be Understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inhibiting interleukin-6 (IL-6) production by bone marrow stromal cells in an individual diagnosed with multiple myeloma or a multiple myeloma-related plasmaproliferative disorder, said method comprising administering an inhibitor of interleukin-1β to said individual in an amount effective to inhibit the production of IL-6 by said bone marrow stromal cells, wherein said inhibitor of interleukin-1β is an anti-IL-1β antibody, an interleukin-1 receptor antagonist (IL-1ra), a soluble IL-1 receptor (sIL-1R), or an IL-1 TRAP.

2. A method of inhibiting interleukin-6 induced myeloma cell proliferation in an individual diagnosed with multiple myeloma or a multiple myeloma-related plasmaproliferative disorder, said method comprising administering an inhibitor of interleukin-1β to said individual in an amount sufficient to inhibit myeloma cell proliferation, wherein said inhibitor of interleukin-1β is an anti-IL-1β antibody, an interleukin-1 receptor antagonist, a soluble IL-1 receptor, or an IL-1 TRAP.

3. The method of claim 1, wherein said multiple myeloma-related plasmaproliferative disorder is monoclonal gammopathy of undetermined significance.

4. The method of claim 1, wherein said inhibitor of IL-1β is an anti-IL-1β antibody.

5. The method of claim 2, wherein said multiple myeloma-related plasmaproliferative disorder is monoclonal gammopathy of undetermined significance.

6. The method of claim 1, wherein said inhibitor of IL-1β is an IL-1ra.

7. The method of claim 2, wherein said inhibitor of IL-1β is an anti-ILβ antibody.

8. The method of claim 2, wherein said inhibitor of IL-1β is an IL-1ra.

9. The method of claim 1, wherein said inhibitor of IL-1β is a sIL-1R type I.

10. The method of claim 1, wherein said inhibitor of IL-1β is 1 a sIL-1R type II.

11. The method of claim 2, wherein said inhibitor of IL-1β is a sIL-1R type I.

12. The method of claim 2, wherein said inhibitor of IL-1β is a sIL-1R type II.

13. The method of claim 1, wherein said inhibitor of IL-1β is an IL-1 TRAP.

14. The method of claim 1, wherein said multiple myeloma-related plasmaproliferative disorder is smoldering multiple myeloma.

15. The method of claim 14, wherein said inhibitor of IL-1β is an IL-1ra.

16. The method of claim 14, wherein said inhibitor of IL-1β is an anti-IL-1β antibody.

17. The method of claim 14, wherein said inhibitor of IL-1β is an IL-1 TRAP.

18. The method of claim 1, wherein said multiple myeloma-related plasmaproliferative disorder is indolent multiple myeloma.

19. The method of claim 18, wherein said inhibitor of IL-1β is an IL-1ra.

20. The method of claim 18, wherein said inhibitor of IL-1β is an anti-IL-1β antibody.

21. The method of claim 18, wherein said inhibitor of IL-1β is an IL-1 TRAP.

22. The method of claim 1, wherein said inhibitor of IL-1β is administered subcutaneously.

23. The method of claim 1, wherein said inhibitor of IL-1β is administered intravenously.

24. The method of claim 2, wherein said inhibitor of IL-1β is an IL-1 TRAP.

25. The method of claim 2, wherein said multiple myeloma-related plasmaproliferative disorder is smoldering multiple myeloma.

26. The method of claim 25, wherein said inhibitor of IL-1β is an IL-1ra.

27. The method of claim 25, wherein said inhibitor of IL-1β is an anti-IL-1β antibody.

28. The method of claim 25, wherein said inhibitor of IL-1β is an IL-1 TRAP.

29. The method of claim 2, wherein said multiple myeloma-related plasmaproliferative disorder is indolent multiple myeloma.

30. The method of claim 29, wherein said inhibitor of IL-1β is an IL-1ra.

31. The method of claim 29, wherein said inhibitor of IL-1β is an anti-IL-1β antibody.

32. The method of claim 29, wherein said inhibitor of IL-1β is an IL-1 TRAP.

33. The method of claim 2, wherein said inhibitor of IL-1β is administered subcutaneously.

34. The method of claim 2, wherein said inhibitor of IL-1β is administered intravenously.

* * * * *

UNITED STATES PATENT AND TRADEMARK OFFICE
CERTIFICATE OF CORRECTION

PATENT NO. : 7,820,167 B2  
APPLICATION NO. : 11/043209  
DATED : October 26, 2010  
INVENTOR(S) : Kathleen A. Donovan Page 1 of 1

It is certified that error appears in the above-identified patent and that said Letters Patent is hereby corrected as shown below:

On the title page, item [54] & col. 1, line 1;
(Title), please delete "IL 1-β" and insert --IL-1β--, therefor.

Column 1 (Other publications), line 10, please delete "anatagonist" and insert --antagonist--, therefor.

Column 1 (Other publications), line 15, please delete "gammapathies" and insert --gammopathies--, therefor.

Column 13, line 51, please delete "anti-ILβ" and insert --anti-IL-1β--, therefor.

Column 14, line 2, after "is" please delete "1".

Signed and Sealed this
Twenty-seventh Day of December, 2011

David J. Kappos
*Director of the United States Patent and Trademark Office*